United States Patent
Panzer et al.

(10) Patent No.: US 8,105,255 B2
(45) Date of Patent: Jan. 31, 2012

(54) ORTHOSIS FOR CORRECTING THE POSITION OF A BODY JOINT

(75) Inventors: Dominique Panzer, Zeulenroda-Triebes (DE); Peter Sachs, Vogtlandisches Oberland (DE); Michel Vanfleteren, Tonisvorst (DE)

(73) Assignee: Bauerfeind AG, Zeulenroda (DE)

( * ) Notice: Subject to any disclaimer, the term of this patent is extended or adjusted under 35 U.S.C. 154(b) by 248 days.

(21) Appl. No.: 12/372,488

(22) Filed: Feb. 17, 2009

(65) Prior Publication Data

US 2009/0216164 A1 Aug. 27, 2009

(30) Foreign Application Priority Data

Feb. 15, 2008 (DE) .................. 10 2008 009 273

(51) Int. Cl.
*A61F 5/00* (2006.01)
(52) U.S. Cl. ................. 602/16; 602/23; 602/26
(58) Field of Classification Search .............. 602/16, 602/26, 27, 5, 19, 12, 20, 23, 24, 25; 128/882; 36/156, 157
See application file for complete search history.

(56) References Cited

U.S. PATENT DOCUMENTS

| | | | | |
|---|---|---|---|---|
| 5,885,235 A * | 3/1999 | Opahle et al. | .................... | 602/16 |
| 5,938,629 A | 8/1999 | Bloedau | | |
| 5,997,493 A * | 12/1999 | Young | .............................. | 602/16 |
| 6,254,559 B1 | 7/2001 | Tyrrell | | |
| 7,322,951 B2 * | 1/2008 | Reinhardt | ........................ | 602/16 |

FOREIGN PATENT DOCUMENTS

| | | |
|---|---|---|
| DE | 10 2004 008 909 A1 | 9/2005 |
| DE | 20 2005 010 491 U1 | 12/2006 |
| EP | 1 568 337 A1 | 8/2005 |

* cited by examiner

*Primary Examiner* — Patricia Bianco
*Assistant Examiner* — George N Phillips
(74) *Attorney, Agent, or Firm* — Birch, Stewart, Kolasch & Birch, LLP

(57) ABSTRACT

An orthosis including arms held in place on body parts by a respective fastening member and interconnected by a pivot joint adjacent to a body joint. For bending of the body parts required during normal movement, the pivot joint is formed by a central adjusting ring bordered by both arms. One arm includes an axle ring which is coaxial to the adjusting ring. The other arm includes a ring bearing, which is eccentric to the axle ring. The ring bearing is pivotable with respect to a rotational plane of the axle ring by rotating the adjusting ring in such a way and at such an angle that the arm, supported by the ring bearing in conjunction with the body part retained by it, assumes a pivoting position of this body part depending on the rotation angle of the adjusting ring in relation to the arm connected to the axle ring.

15 Claims, 5 Drawing Sheets

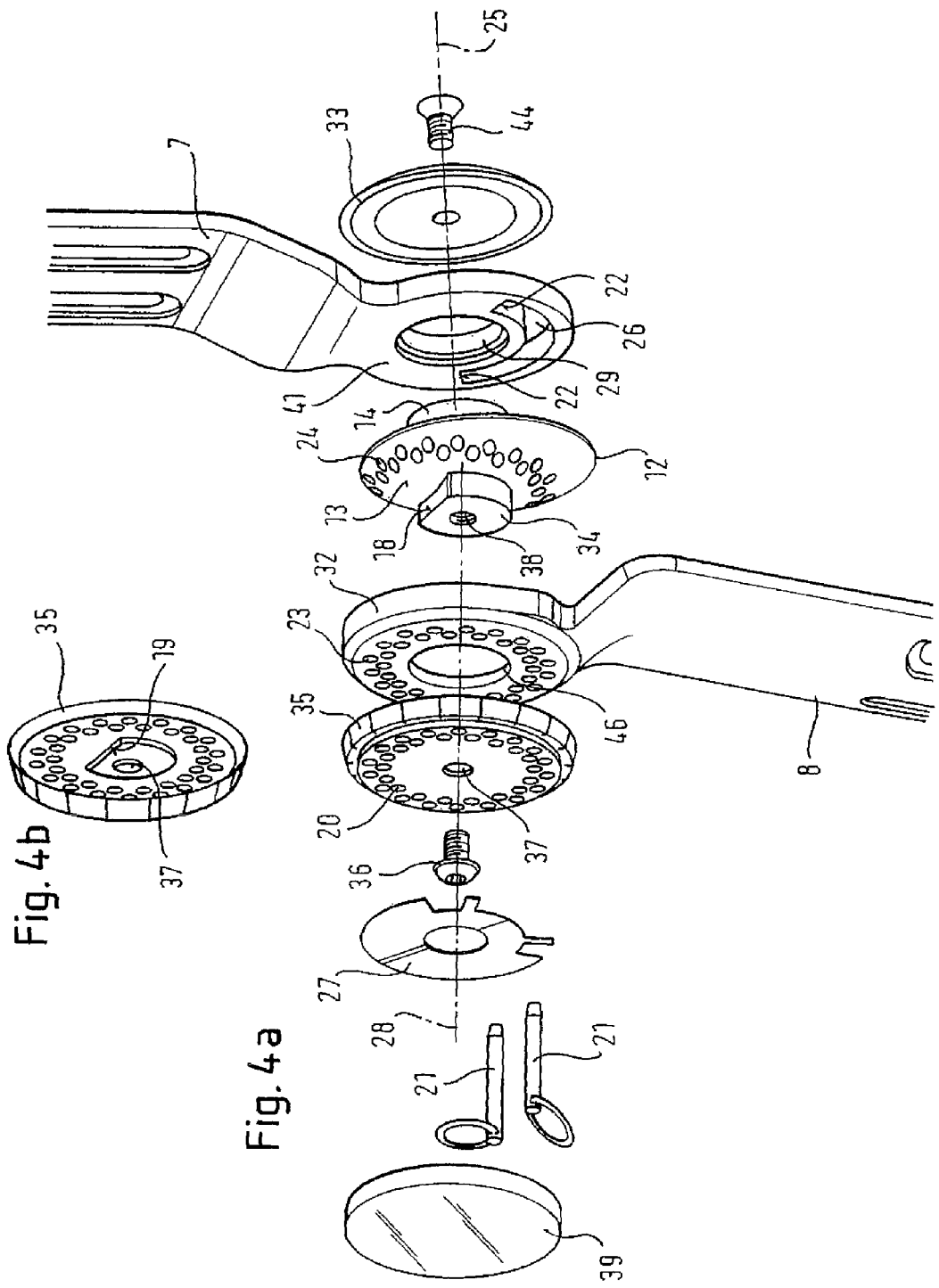

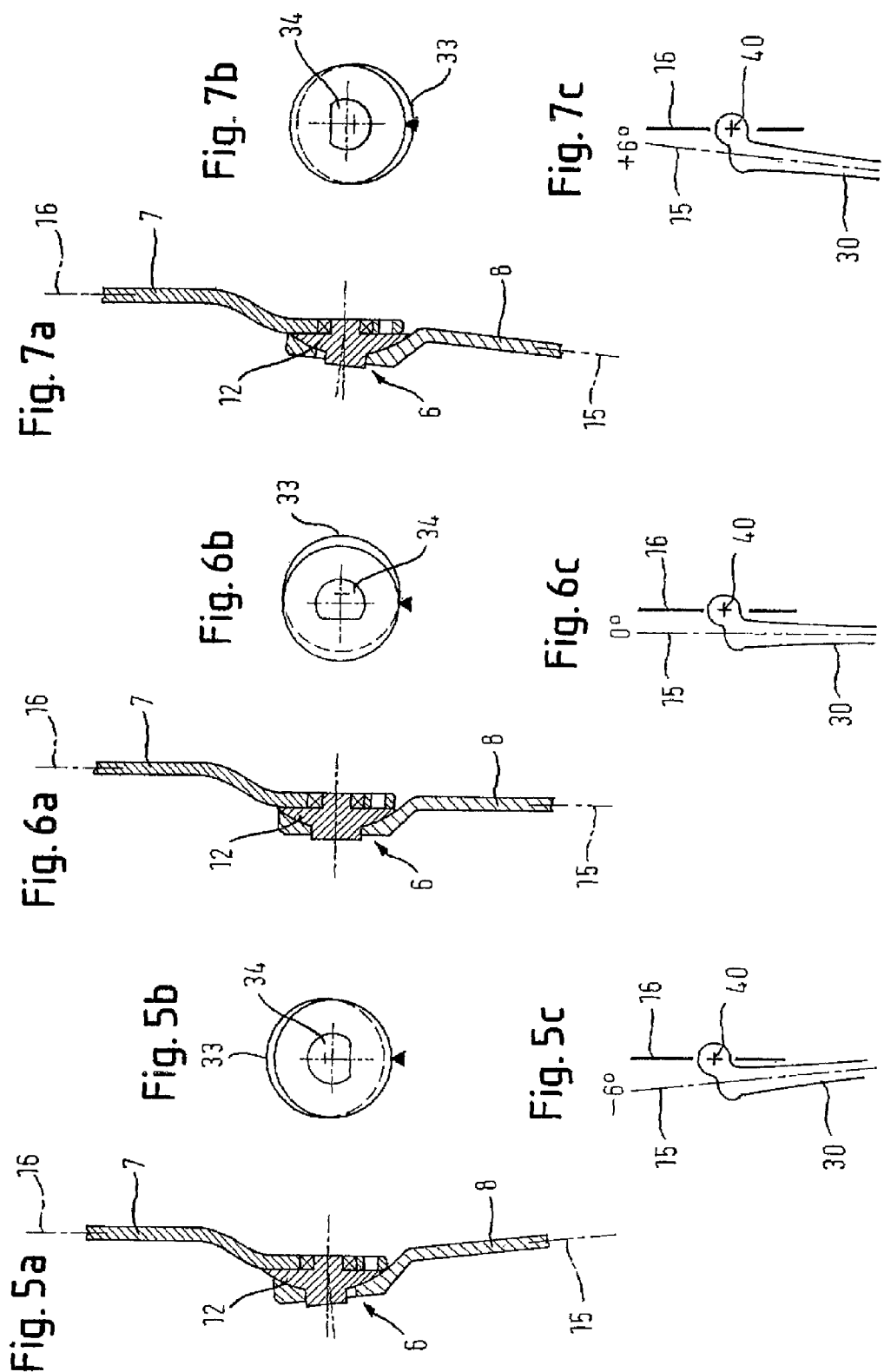

ORTHOSIS FOR CORRECTING THE POSITION OF A BODY JOINT

CROSS-REFERENCE TO RELATED APPLICATIONS

The present application claims priority under 35 USC 119 to German Patent Application No. 10 2008 009 273.8 filed on Feb. 15, 2008 the entire contents of which are hereby incorporated by reference.

BACKGROUND OF THE INVENTION

1. Field of the Invention

The invention relates to an orthosis for correcting the position of a two-jointed body joint, which extends across the two body parts interconnected by the body joint, the orthosis being provided with two arms, which are held in place on the body parts by a respective fastening means and are interconnected by a pivot joint adjacent to the body joint.

2. Description of Background Art

For bending of the body parts required during normal movement, the pivot joint is formed by a central adjusting ring bordered by both arms, which for the one arm has an axle ring, which is coaxial to the adjusting ring, and for the other arm has a ring bearing, which is eccentric to the axle ring. The rotational plane of the ring bearing is pivotable with respect to the rotational plane of the axle ring by rotating the adjusting ring in such a way and at such an angle that the arm, supported by the ring bearing in conjunction with the body part retained by it, assumes a pivoting position of this body part as opposed to the stretched normal position, depending on the rotation angle of the adjusting ring in relation to the arm connected to the axle ring, An orthosis such as this is illustrated and described in EP 1 568 337 B1. The object of this orthosis is to correct and stabilize the position of the body joint, the joint being a big toe or a knee joint, for example.

In the known orthosis, the two joints connecting the body joint are connected to the arms forming the orthosis, which are interconnected in the pivot joint. More specifically, the pivot joint is formed by the central adjusting ring, which includes the axle ring for the one arm and the ring bearing for the other arm. An orthosis design is thereby, used, wherein the ring bearing is mounted eccentrically with respect to the axle ring and coaxially with respect to the adjusting ring. As a result, the rotational plane of the ring bearing and the rotational plane of the axle ring are pivoted in relation to one another, depending on the adjustment of the adjusting ring.

SUMMARY AND OBJECTS OF THE INVENTION

It is the object of an embodiment of the present invention to form the joint of the orthosis such that with respect to its angle, the respective rotational plane of the two arms is selectively adjustable, and that the adjustment of the arms in relation to one another can be executed in a simple and clearly laid out manner.

The objective of an embodiment of the present invention is achieved such that the adjusting ring is attached in a rotationally fixed connection to an end plate covering the ring bearing toward the outside via a coupling feeding through the ring bearing. The end plate allowing the adjustment of the rotational plane of one arm to the rotational plane of the other arm.

Due to this design, by merely rotating the end plate, the pivot joint as such is adjusted in a way that is most beneficial and/or necessary for a particular patient to correct and stabilize the body joint in question. The arms of the orthosis, with the movement in the desired rotational planes enforced by the setting of the adjusting ring, are aligning the body joint correspondingly during movement. The adjustment of the pivot joint can thereby be done in a simple way such that the end plate is put in the desired and/or required rotational position with the result that via the adjusting ring, the two bearings for the two arms of the orthosis, that is, the axle ring and the ring bearing, are properly adjusted.

In order to allow the maximal adjustment of the two arms, and thus the afflicted body parts, the pivot joint as described above can be provided with a special design. In this design, the end plate for accommodating driving pins is provided with a plurality of openings, which are aligned with corresponding openings in the arm end and in the adjusting ring, and the driving pins inserted in the openings extend into an elongated hole, which partially surrounds the axis of the axle ring in a circular arc, the ends of which form stops for the driving pins to avoid further rotation of the adjusting ring.

To rotate the two arms with respect to one another, the end plate is rotated with respect to the ring bearing, which is restricted with respect to the maximal rotation angle by inserting driving pins such that the pins, which extend through the entire pivot joint, roam to the elongated hole surrounding the axis of the axle ring in a circular arc to terminate at the ends of the elongated hole, which thus serve as stops for the maximal rotation of the arms.

More specifically, the end plate is provided with a removable annular dial scale, which makes it possible to read the leeway the arms have for moving, which is determined by the inserted driving pins.

The rotational angle of one arm in relationship to the other is hereby determined by the pins inserted in the adjusting ring, which extend all the way to the axle ring area of the adjusting ring, and which then extend into the elongated hole, where at the ends of the elongated hole they encounter stops, which define the rotation angle of the respective arm. As a result of this design, a fixed angular connection between the axle ring and the end plate via the pins is achieved. Thus, the design is a sturdy design.

Further scope of applicability of the present invention will become apparent from the detailed description given hereinafter. However, it should be understood that the detailed description and specific examples, while indicating preferred embodiments of the invention, are given by way of illustration only, since various changes and modifications within the spirit and scope of the invention will become apparent to those skilled in the art from this detailed description.

BRIEF DESCRIPTION OF THE DRAWINGS

The present invention will become more fully understood from the detailed description given hereinbelow and the accompanying drawings which are given by way of illustration only, and thus are not limitative of the present invention, and wherein:

FIGS. 4a and 4b are perspective and exploded views of the pivot joint and its components as illustrated in FIG. 2;

FIGS. 5a, 5b, 5c are sectional views of the basic components of the pivot joint in its first extreme position;

FIGS. 6*a*, 6*b*, 6*c* illustrate the same pivot joint in its intermediate position;

FIGS. 7*a*, 7*b*, 7*c* illustrate the same pivot joint in its other extreme position;

DETAILED DESCRIPTION OF THE PREFERRED EMBODIMENTS

Figure 1:
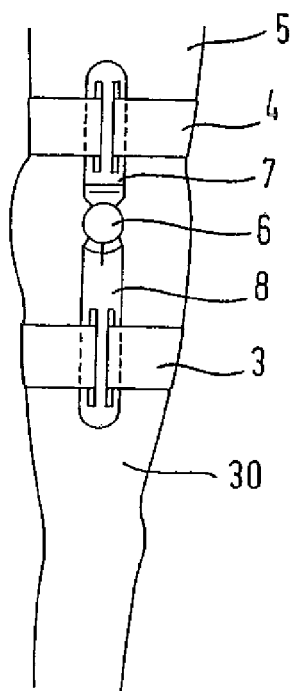
FIG. 1 shows an exemplary orthosis attached laterally to the human body at level with the hip joint.

FIG. 1 shows the orthosis with its pivot joint 6 and the two arms 7 and 8 in a basic illustration. Arm 7 is attached to the body part 5 by fastening means 4 designed as a tightening strap, the body part in this example being a human hip. The arm 8 is fastened at the thigh 30 by fastening means 3, in this instance a tightening strap. The pivot joint 6 of the orthosis is thereby held in position that is level with the hip joint, which is stabilizingly retained in a desired position by the orthosis.

Figure 2:
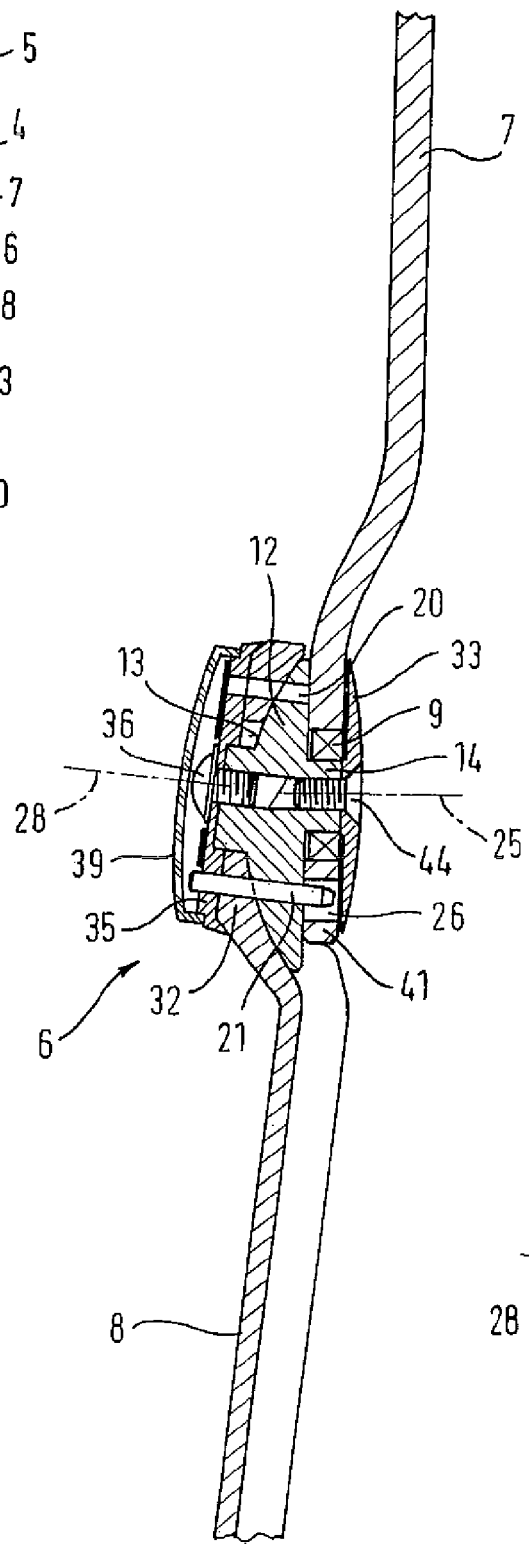
FIG. 2 shows a cross section the orthosis with the pivot joint and the two arms.
Figure 9:
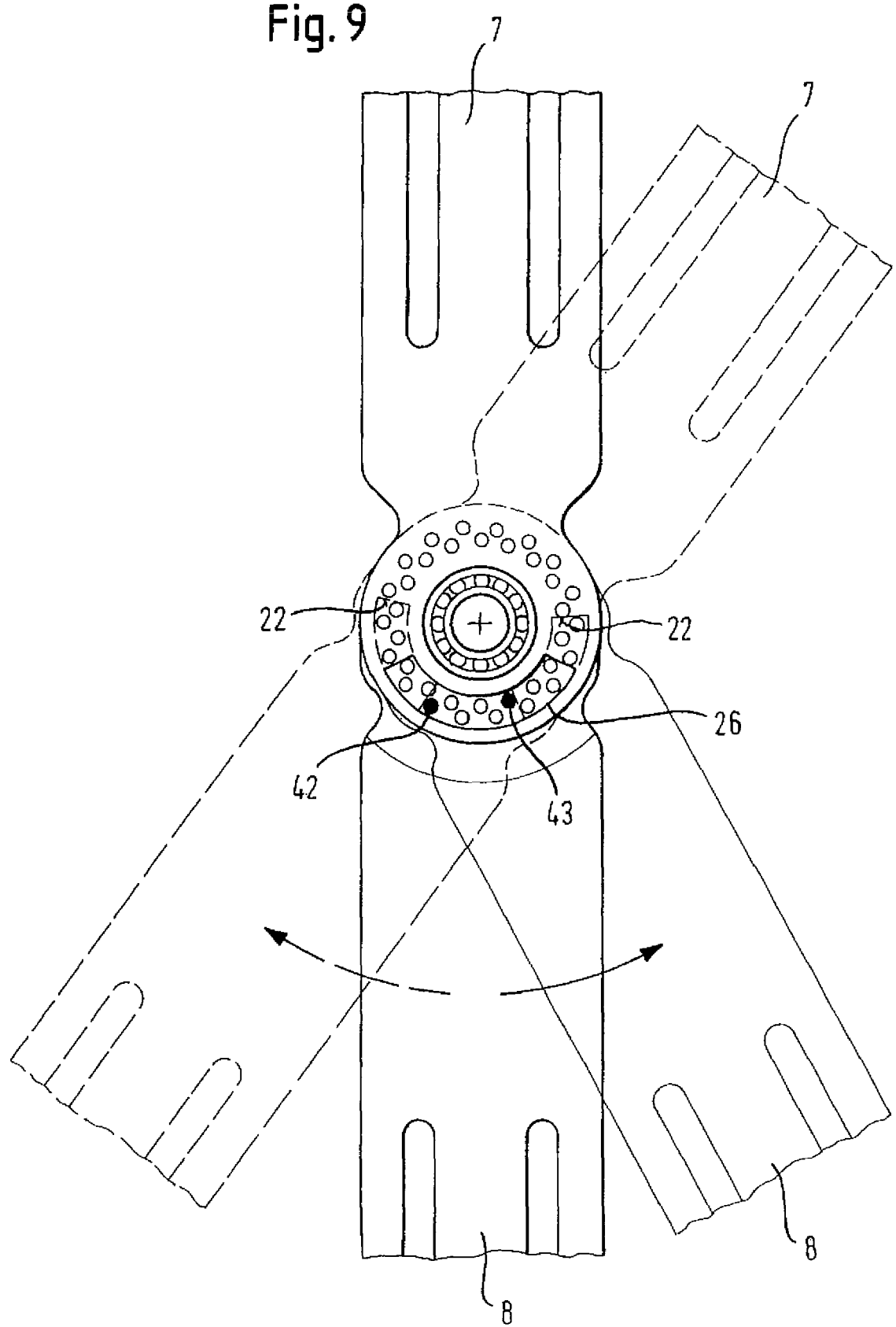
FIG. 9 illustrates the pivot joint of FIG. 8 illustrating a deviated position as a result of the bending of the afflicted body joint.

FIG. 2 shows the orthosis itself in a cross-sectional view, that is, its pivot joint 6 with the two arms 7 and 8 protruding from the pivot joint 6. In its internal part, the pivot joint 6 accommodates the adjusting ring 12, which causes two axes 25 and 28 to be formed at an angle of about 6° to one another. The adjusting ring 12 comprises two bearings for the two arms 7 and 8, that is, the axle ring 14 provided with a ball bearing 9 for arm 7, and the ring bearing 13 formed by the flatly curved conical surface of the adjusting ring 12. The axle ring 14 is comprised of a cylindrical projection of the adjusting ring 12 extending coaxially to the axis 25. Due to this positioning of arm 7 on the axle ring 14 formed with the ball bearing 9, a rotational mobility of arm 7 is achieved, as indicated in FIG. 9. The ring bearing 13 located on the other side of the adjusting ring 12 for arm 8 defines the convex rounded shape of the surface of the adjusting ring 12, on which the arm end 32 being of corresponding concave rounded shape is seated solidly, and which, due to the conicity of the curvature, is also rotatable, that is, around axis 28, which inclines by about 6 degrees in relation to the axis 25 of the axle ring 14, as can be clearly seen in FIG. 2.

As a result of this construction, the arm 7 is pivotable with respect to the adjusting ring 12 (see FIG. 9), and the arm 8 guided through the ring bearing 13 is likewise pivotable, whereby the two rotational planes of arms 7 and 8 (see FIGS. 5*c*, 6*c* and 7*c*) are more or less inclined towards one another, and in an intermediate position also extend in parallel to one another. The position of arms 7 and 8 to one another as illustrated in FIG. 2 is thereby corresponding to the position shown in FIG. 7*c* as a basic one.

The required structural cohesion of the pivot joint 6 illustrated in FIG. 2 is warranted by the following components:

On the side of the adjusting ring 12 that supports the axle ring 14 for bearing the arm 7, the end plate 33 is fastened by screw 44, the screw extends coaxially to axis 25. With the end plate 33 screwed down, the arm 7 is securely positioned at the adjusting ring 12, that is, maintaining a minimal play in relation to the adjusting ring 12, so that the arm 7 is easily pivotable around the axle ring 14, and thus around the axis 25.

On the side opposite the adjusting ring 12, the arm end 32 of arm 8 is solidly pressed against the curved surface of the adjusting ring 12 by an additional end plate 35, whereby the curved surface forms the ring bearing 13 for the rotation of arm 8, which allows the rotation of the arm end 32 due to the conical shape of the curved surface. The end plate 35 is pressed by the screw 36 in the direction of the adjusting ring 12, whereby the screw 36 is adjusted such that with a minimal friction of the arm end 32, the arm 8 is easily rotated with respect to the screw 36 extending coaxially with axis 28.

Figure 8:
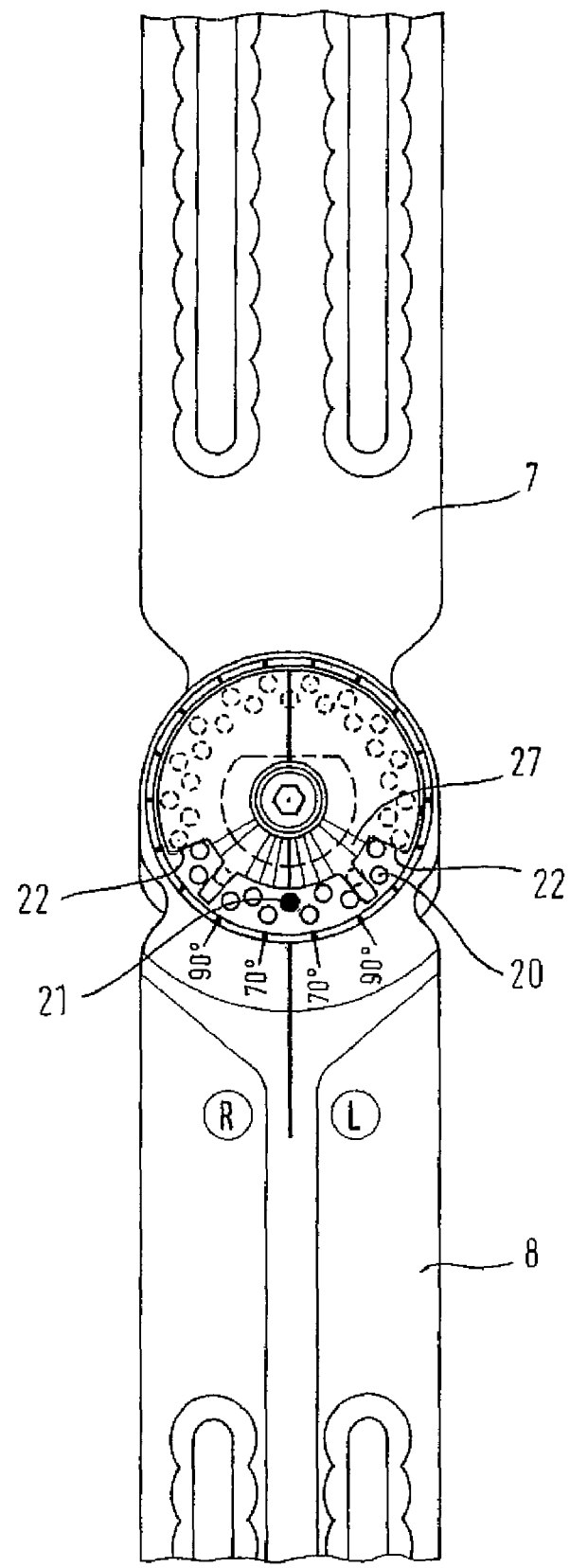
FIG. 8 is a top view of the pivot joint and its two arms through the transparent end plate.

On the end plate 35, the annular dial scale 27 is fastened, that is, mounted, which is described in more detail therebelow in connection with FIGS. 4 and 8. In order to protect the annular dial scale 27 from contamination, the protective cap 39 is fitted onto the end plate 35, which prevents the driving pins 21 from falling out (see FIG. 4).

The adjusting ring 12 is provided with a circle of openings 20, which are described in more detail in connection with FIG. 4. Into the openings, driving pins 21 can be inserted, which, as shown in FIG. 2, extend through the end plate 35, the arm end 32 of arm 8, the adjusting ring 12, and protrude into an elongated hole 26, which also will be discussed in more detail in connection with FIG. 4.

Figure 3:
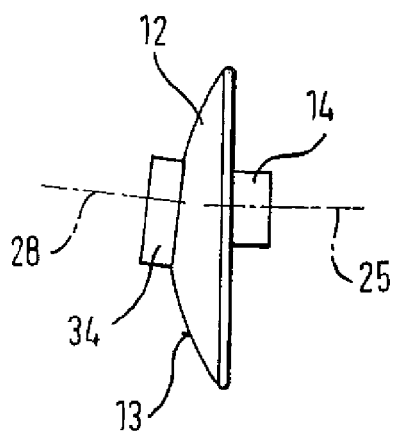
FIG. 3 shows the adjusting ring embedded in the pivot joint.

To more clearly illustrate the design of adjusting ring 12, it is illustrated separately in an uncut side view in FIG. 3. Shown on the adjusting ring 12 is the axle ring 14 formed as an annular projection, which extends coaxially to the axis 25 of adjusting ring 12. On the other side of the adjusting ring 12, the ring bearing 13 formed by a conically extending curvature, and cone axis 28 are illustrated, which is pivoted by an angle of about 6° in relationship to the axis 25. As a result of this mutual rotation of axes 25 and 28, the arm 7 positioned on the axle ring 14 (see FIG. 2) passes through a rotational plane (see FIGS. 5*c*, 6*c*, 7*c*), which is slightly pivoted with respect to the rotational plane of the arm 8 positioned on the ring bearing 13, corresponding to the rotational planes 15 for arm 8 and the rotational plane 16 for arm 7 illustrated in FIGS. 5*c*, 6*c* and 7*c*. In addition, coaxially to the axis 28, a projection 34 is provided, the function of which is described in more detail in connection with FIGS. 4*a* and 4*b*.

In FIG. 4*a*, the pivot joint 6 according to FIG. 2 is rendered with all its components in an exploded view. FIG. 4*a* shows that the central component of the pivot joint 6 is the adjusting ring 12 (see FIG. 3), on one side of which the axle ring 14 is formed as pivot bearing for arm 7, and the conically curved ring bearing 13 is formed as a bearing for arm 8, whereby the projection 34 protrudes from the ring bearing 13, with the projection extending coaxially to the axis 28, with the exception of the flat section 18. The flat section 18 will be described in more detail therebelow.

Mounted on the axle ring 14 is the arm end 41 having a hole 29, which fits the axle ring 14, whereby the ball bearing illustrated in FIG. 2 is inserted therebetween in its appropriate location (not shown in FIG. 4*a* or 4*b*), so that the arm 7 can be pivoted around axis 25, which also extends coaxially through axle ring 14. Furthermore, the arm end 41 includes the elongated hole 26, which surrounds the axis 25 in a circular arc, which will be discussed in more detail therebelow. The arm end 41 is provided by the end plate 33, which in conjunction with screw 44, which can be screwed into the adjusting ring 12, holds the previously mentioned components together and presses firmly onto the adjusting ring 12.

On the other side of the adjusting ring 12, the projection 34 is provided, which, with the exception of the flat section 18, includes a cylindrical part, the axis of which is formed by the axis 28. The arm end 32 of arm 8 is mounted on the projection 34 by way of hole 46 made to fit the projection 34, whereby the lateral surface of the arm end 32 facing the curved surface of the adjusting ring 12 as illustrated in FIG. 4*a* is seated solidly and rotatably with respect to the adjusting ring 12. The arm end 32 is then covered by end plate 35, which is provided with a through hole 37, through which screw 36 can be fed to fasten the end plate 35 and the arm end 32 to the adjusting ring 12, which is provided with a threaded hole 38 coaxially located in the area of its projection 34. By tightening the screw 36, the connection with the ring bearing 13 for arm 8, which is formed by the curved surface of the adjusting ring 12, is then achieved, as illustrated in FIG. 2.

By rotating the end plate 35, the adjusting ring 12 is also rotated around its axis 25, which results in a displacement of the ring bearing 13, as is necessary for the adjustment of the two arms 7 and 8 to one another, and which will be described in more detail in connection with FIGS. 5a, 6a and 7a. The coupling between end plate 35 and adjusting ring 12 is accomplished by providing the projection 34 with the flat section 18, which matches the flat part 19. This is illustrated in FIG. 4b, which shows the end plate 35 in a position, in which the side facing the arm end 32 is visible. In this way, a coupling between the end plate 35 with the flat part 19 and the flat part 18 on the projection 34 of adjusting ring 12 is achieved. As a result of this coupling, the adjusting ring 12 can be adjusted at will by rotating the end plate 35, whereby the axle ring 14 of adjusting ring 12 rotates freely in hole 29 of arm end 41, thus also displacing axis 28 with respect to axis 25, resulting in a suitable desired displacement of the rotational planes of arms 7 and 8 to one another. This is described in more detail in FIGS. 5a to 7c.

In order for one of the two arms 7 or 8 to receive an optional fixed adjustment to the adjusting ring 12, the end plate 35, the arm end 32, and the adjusting 12, are respectively provided with a circle of openings 20, 23 and 24, which, when properly adjusted, align these three components of the pivot joint 6 with one another, and can thus be interlocked by the driving pins 21 inserted in the openings. This locking mechanism is shown in FIG. 2 based on driving pin 21 illustrated there. If the driving pins 21 shown individually in FIG. 4a are inserted in the openings 20, 23 and 24, then the arm 8, with respect to its rotational position against end plate 35 and the adjusting ring 12, which is rotatably coupled with the end plate, is connected so that a rotating of the arm 8 will also entail a corresponding rotation of end plate 35 and adjusting ring 12. This function and the result thereof will also be discussed in more detail in connection with FIGS. 5a to 7c.

As illustrated in FIGS. 4a and 4b, the annular dial scale 27, which can be placed on the end plate 35, is illustrated, which, as discussed in FIG. 2, is placed on the outer surface of end plate 35 and is rotated with said end plate. The adjustment of the orthosis based on a rotational position indicated on the annular dial scale 27 is described in more detail therebelow in connection with FIG. 8.

FIG. 4a also shows the protective cap 39, which is made of transparent material, can be snapped onto the end plate 35, and through which the annular dial scale 27 located therebelow is readable.

In FIGS. 5a, 5b, 5c, 6a, 6b, 6c, 7a, 7b and 7c, simplified illustrations of pivot joint 6 with both arms 7 and 8 in different angular positions of the rotational planes 15 and 16 of arms 8 and 7 are shown, wherein in FIGS. 5b, 6b and 7b the projection 34 with coaxial adjusting ring 12 and end plate 33, respectively, are shown with their rims. According to FIG. 5a, by adjusting the adjusting ring 12, an angle of 6° of rotational planes 16 and 15 of arms 7 and 8 is achieved, an angle of 0° as a result of the adjustment according to FIG. 6a is achieved, and an angle of 6° as a result of the adjustment according to FIG. 7a is achieved, wherein the difference between the adjustments of FIG. 5a and FIG. 7a is such that in the first instance, the external body part 30 (FIG. 1) is pressed inwards, whereas in the adjustment according to FIG. 7a, the same body part is pressed outwards. To illustrate this, the rotational angles −6°, 0°, +6° of the adjusting ring 12, which are indicated by a corresponding position of the flat part 18 on the adjusting ring, are also shown in FIGS. 5b, 6b and 7b. To demonstrate the effect of these adjustments, a hip joint 40 is shown in FIGS. 5c, 6c and 7c, which in FIG. 5c shows a 6° inward angle to the rotational plane 16 of an upper body, and in FIG. 7c shows a 6° outward angle, whereas FIG. 6c illustrates the standard case, in which the rotational plane 15 is 0°.

FIG. 8 shows a top view of the orthosis with pivot joint 6 and arms 7 and 8, with the annular dial scale 27 being visible, which shows the openings 20 in end plate 35. In one of the openings 20 driving pin 21 is shown, the end of which, as shown in FIG. 2, can move freely in the elongated hole 26 of arm end 32 during the rotation of the arms 7 and 8 against each other, until the driving pin 21 encounters the end of the elongated hole 26, which forms the stop 22, so that a maximal rotation possibility of one arm against the other occurs, at which point the driving pin 21 comes up against one of the two stops 22, respectively.

FIG. 9 shows an illustration matching the illustration in FIG. 8, with the sole exception that instead of one driving pin 21 (see FIG. 8), two driving pins 42, 43, are inserted resulting in more restricted room for movement, because with one rotational angle, the driving ping 42 comes up against the one of stop 22, and during rotation in the opposite direction, the driving pin 43 comes up against the other stop 22, thus limiting the movement of one arm against the other one correspondingly.

The invention being thus described, it will be obvious that the same may be varied in many ways. Such variations are not to be regarded as a departure from the spirit and scope of the invention, and all such modifications as would be obvious to one skilled in the art are intended to be included within the scope of the following claims.

What is claimed is:

1. An orthosis for the correction of the position of a two-jointed body joint extending across the two body parts (5, 30) interconnected by the body joint, the orthosis being provided with first and second arms (7, 8), which are held in position on the body parts (5, 30) by a respective fastening means (3, 4) and are interconnected by a pivot joint (6) adjacent to the body joint, the pivot joint (6) being formed by a central adjusting ring (12) bordered by the first and second arms (7, 8) for bending the body parts (5, 30) necessary for normal movement, said pivot joint comprising:

an axle ring (14) being coaxial with respect to the central adjusting ring (12) for one arm; and a ring bearing (13) being eccentric with respect to the axle ring (14) for the other arm, the rotational plane (15) of which is pivotable with respect to the rotational plane (16) of the axle ring (14) by rotating the central adjusting ring (12) in such a way at such an angle that the arm (8), supported by the ring bearing (13) and in conjunction with the body part (30) retained by it, assumes a pivoting position of this body part (30) as opposed to the stretched normal position, depending on the rotation angle on the central adjusting ring (12) in relation to the first arm (7) connected to the axle ring (14);

wherein the central adjusting ring (12) has a rotationally fixed connection with an end plate (35) covering the ring bearing (13) toward the outside, via a coupling (18, 19) feeding through the ring bearing (13), said end plate (35) allowing the adjustment of the rotational plane (15) the second arm (8) to the rotational plane (16) of the first arm (7), wherein the ring bearing (13) includes a single projection (34) facing said end plate (35), the projection (34) having a peripheral side having a semi-circular portion and a flat section (18), the coupling (18,19) being formed by the flat section (18) on the peripheral side of the projection (34) which matches a flat part (19) of the end plate (25).

2. The orthosis according to claim 1, wherein the end plate (35) for accommodating driving pins (21) is provided with a plurality of openings (20), which are aligned with corresponding openings (23, 24) in the arm end (32) and in the adjusting ring (12), the driving pins (21) inserted into the openings (20, 23, 24) extending all the way to an elongated hole (26) partially surrounding the axis (25) of the axle ring (14) in a circular arc, the ends of which form stops (22) for the driving pins (21) to avoid further rotation of the central adjusting ring (12).

3. The orthosis according to claim 2, wherein the end plate (35) is provided with a removable annular dial scale (27), on which room for movement of the first and second arms (7, 8) determined by the driving pins (21) can be read.

4. The orthosis according to claim 1, wherein the end plate (35) is provided with a removable annular dial scale (27), on which room for movement of the first and second arms (7, 8) determined by the driving pins (21) can be read.

5. The orthosis according to claim 1, wherein an arc of the semi-circular portion of the projection (34) is greater than 180°.

6. The orthosis according to claim 1, wherein the end plate (35) has an inner surface shaped as a truncated conical surface which is adapted to fit over an outer truncated conical surface of an end (32) of the second arm (8).

7. The orthosis according to claim 1, wherein the axle ring (14) and the single projection (34) have axes which are non-coaxial.

8. An orthosis for the correction of the position of a two-jointed body joint extending across the two body parts (5, 30) interconnected by the body joint, the orthosis being provided with first and second arms (7, 8), which are held in position on the body parts (5, 30) by a respective fastening means (3, 4) and are interconnected by a pivot joint (6) adjacent to the body joint, the pivot joint (6) being formed by a central adjusting ring (12) bordered by the first and second arms (7, 8) for bending the body parts (5, 30) necessary for normal movement, said pivot joint comprising:
    an axle ring (14) being coaxial with respect to the central adjusting ring (12) for one arm; and
    a ring bearing (13) being eccentric with respect to the axle ring (14) for the other arm, the rotational plane (15) of which is pivotable with respect to the rotational plane (16) of the axle ring (14) by rotating the central adjusting ring (12) in such a way at such an angle that the arm (8), supported by the ring bearing (13) and in conjunction with the body part (30) retained by it, assumes a pivoting position of this body part (30) as opposed to the stretched normal position, depending on the rotation angle on the central adjusting ring (12) in relation to the first arm (7) connected to the axle ring (14);
    wherein the central adjusting ring (12) has a rotationally fixed connection with an end plate (35) covering the ring bearing (13) toward the outside, via a coupling (18, 19) feeding through the ring bearing (13), said end plate (35) allowing the adjustment of the rotational plane (15) the second arm (8) to the rotational plane (16) of the first arm (7),
    wherein the ring bearing (13) includes a single projection (34) facing said end plate (35), the projection (34) having a periphery having a flat section (18),
    the coupling (18,19) being formed by the flat section (18) on the periphery of the projection (34) which matches a flat part (19) of the end plate (35),
    wherein the ring bearing (13) extends outwardly in a radial direction further than a periphery of the projection (34) and a periphery of the axle ring (14).

9. The orthosis according to claim 8, wherein the end plate (35) for accommodating driving pins (21) is provided with a plurality of openings (20), which are aligned with corresponding openings (23, 24) in the arm end (32) and in the adjusting ring (12), the driving pins (21) inserted into the openings (20, 23, 24) extending all the way to an elongated hole (26) partially surrounding the axis (25) of the axle ring (14) in a circular arc, the ends of which form stops (22) for the driving pins (21) to avoid further rotation of the central adjusting ring (12).

10. The orthosis according to claim 9, wherein the end plate (35) is provided with a removable annular dial scale (27), on which room for movement of the first and second arms (7, 8) determined by the driving pins (21) can be read.

11. The orthosis according to claim 8, wherein the end plate (35) is provided with a removable annular dial scale (27), on which room for movement of the first and second arms (7, 8) determined by the driving pins (21) can be read.

12. The orthosis according to claim 8, wherein an arc of a semi-circular portion on the periphery of the projection (34) is greater than 180°.

13. The orthosis according to claim 8, wherein the end plate (35) has an inner surface shaped as a truncated conical surface which is adapted to fit over an outer truncated conical surface of an end (32) of the second arm (8).

14. The orthosis according to claim 8, wherein the axle ring (14) and the single projection (34) have axes which are non-coaxial.

15. An orthosis for the correction of the position of a two-jointed body joint extending across the two body parts (5, 30) interconnected by the body joint, the orthosis being provided with first and second arms (7, 8), which are held in position on the body parts (5, 30) by a respective fastening means (3, 4) and are interconnected by a pivot joint (6) adjacent to the body joint, the pivot joint (6) being formed by a central adjusting ring (12) bordered by the first and second arms (7, 8) for bending the body parts (5, 30) necessary for normal movement, said pivot joint comprising:
    an axle ring (14) being coaxial with respect to the central adjusting ring (12) for one arm; and
    a ring bearing (13) being eccentric with respect to the axle ring (14) for the other arm, the rotational plane (15) of which is pivotable with respect to the rotational plane (16) of the axle ring (14) by rotating the central adjusting ring (12) in such a way at such an angle that the arm (8), supported by the ring bearing (13) and in conjunction with the body part (30) retained by it, assumes a pivoting position of this body part (30) as opposed to the stretched normal position, depending on the rotation angle on the central adjusting ring (12) in relation to the first arm (7) connected to the axle ring (14);
    wherein the central adjusting ring (12) has a rotationally fixed connection with an end plate (35) covering the ring bearing (13) toward the outside, via a coupling (18, 19) feeding through the ring bearing (13), said end plate (35) allowing the adjustment of the rotational plane (15) the second arm (8) to the rotational plane (16) of the first arm (7),
    wherein the end plate (35) for accommodating driving pins (21) is provided with a plurality of openings (20), which are aligned with corresponding openings (23) in the arm end (32) of the second arm (8) and corresponding openings (24) in the central adjusting ring (12) which has the rotationally fixed connection with the end plate (35), the driving pins (21) inserted into the openings (20, 23, 24) extending all the way to an elongated hole (26) partially surrounding the axis (25) of the axle ring (14) in a circular arc, the ends of which form stops (22) for the driving pins (21) to avoid further rotation of the central adjusting ring (12) and the end plate (35) which has the rotationally fixed connection to the adjusting ring (12), wherein each of the driving pins (21) is adapted to be accommodated in any of the plurality of different openings (20), an amount of rotation of central adjusting ring (12) is determined by the specific openings (2) in which each of the driving pins (21) is accommodated.

\* \* \* \* \*